(12) United States Patent
Lazdunski et al.

(10) Patent No.: US 6,239,156 B1
(45) Date of Patent: May 29, 2001

(54) METHOD FOR THE PREVENTION OF ISCHEMIC SPINAL CORD INJURY CAUSED BY AORTIC CROSSCLAMPING

(75) Inventors: Michel Lazdunski, Nice; Loic Lang-Lazdunski, Neuilly; Catherine Heurteaux, Antibes, all of (FR)

(73) Assignee: Centre National de la Recherche Scientifique CNRS, Paris (FR)

( * ) Notice: Subject to any disclaimer, the term of this patent is extended or adjusted under 35 U.S.C. 154(b) by 0 days.

(21) Appl. No.: 09/562,699

(22) Filed: Apr. 28, 2000

Related U.S. Application Data

(60) Provisional application No. 60/131,575, filed on Apr. 29, 1999.

(51) Int. Cl.⁷ .................................................. A61K 31/425
(52) U.S. Cl. ............................................................ 514/367
(58) Field of Search ............................................. 514/367

(56) References Cited

U.S. PATENT DOCUMENTS

| | | | |
|---|---|---|---|
| 5,624,945 | * | 4/1997 | Bousseau et al. .................... 514/367 |
| 5,686,475 | * | 11/1997 | Delumeau et al. ................... 514/367 |
| 5,830,907 | * | 11/1998 | Doble et al. ......................... 514/367 |

* cited by examiner

*Primary Examiner*—Raymond Henley, III
(74) *Attorney, Agent, or Firm*—Schnader Harrison Segal & Lewis LLP

(57) ABSTRACT

The present invention pertains to a method for the reduction of glutamate neurotoxicity in pathophysiology of spinal cord injury induced by aortic cross-clamping. The reduction is achieved by the administration of riluzole to a patient, in an amount effective to reduce glutamate neurotoxicity, contemporaneously with aortic cross-clamping. Preferably, the riluzole is administered both prior to and following the aortic cross-clamping. The method is also applicable to reduce the spinal cord injury resulting from ischemia, and for reducing the effects of ischemia on neuronal tissues.

25 Claims, 3 Drawing Sheets

METHOD FOR THE PREVENTION OF ISCHEMIC SPINAL CORD INJURY CAUSED BY AORTIC CROSSCLAMPING

RELATED APPLICATIONS

This application is related to provisional patent application Ser. No. 60/131,575 filed Apr. 29, 1999 entitled Riluzole Prevents Ischemic Spinal Cord Injury Caused By Aortic Crossclamping, by Loic Lang-Lazdunski et al., which is incorporated by reference in its entirety.

FIELD OF THE INVENTION

The present invention relates to the prevention or reduction of glutamate neurotoxicity in the pathophysiology of spinal cord injury induced by aortic crossclamping.

DESCRIPTION OF THE RELATED ART

Spinal cord ischemia remains a devastating complication of thoracoabdominal aortic operations, with paraplegia occurring after as many of 31% of procedures. The cellular and molecular mechanisms that underlie hypoxic-ischemic injury to the spinal cord have not been totally elucidated, but recent studies suggest that the release of excitatory amino acids by ischemic cells into the extracellular space of the central nervous system may contribute substantially to neuronal death.

Glutamate is thought to be the primary excitatory amino acid in the spinal cord, and it may destroy neuronal cells through its actions on N-methyl-D-aspartate (NMDA) and non-NMDA receptors by inducing massive sodium and calcium ion influxes into the cell, resulting in neuronal death. Microdialysis studies have confirmed that an elevation in glutamate level is induced by spinal cord ischemia. Although the neuroprotective effects of NMDA receptor antagonists have been demonstrated both in vitro and in vivo, their pronounced side effects limit their clinical use. Effective NMDA blockers with few side effects have heretofore been unknown.

SUMMARY OF THE INVENTION

The present invention pertains to a method for the reduction of glutamate neurotoxicity in pathophysiology of spinal cord injury induced by aortic cross-clamping. The reduction is achieved by the administration of riluzole to a patient, in an amount effective to reduce glutamate neurotoxicity, contemporaneously with aortic cross-clamping. Preferably, the riluzole is administered both prior to and following the aortic cross-clamping. The method is also applicable to reduce the spinal cord injury resulting from ischemia, and for reducing the effects of ischemia on neuronal tissues.

DETAILED DESCRIPTION OF THE INVENTION

Figure 1:
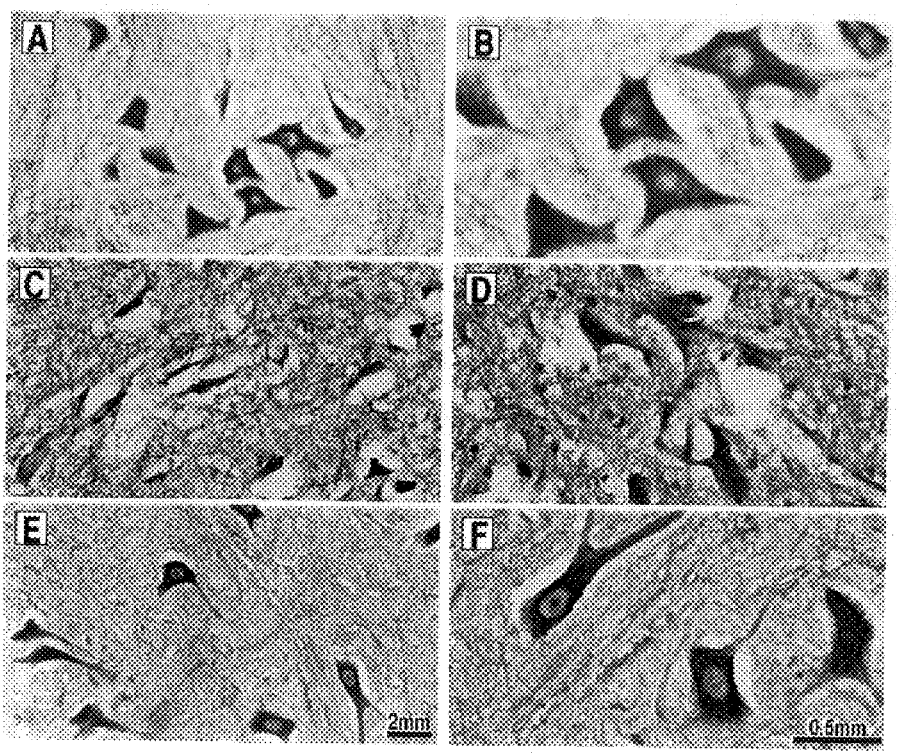
FIG. 1 is a series of photomicrographs of lumbar spinal cord sections stained with Klüver-Barrera stain from sham-operated rabbits (A and B), control (saline-treated) rabbits (C and D) and riluzole-treated rabbits (E and F) that underwent 40 minutes ischemia and five day reperfusion.

Numerous surgical techniques and pharmacologic interventions have been used to reduce the rate of perioperative paraplegia after operations on the thoracoabdominal aorta, but none consistently proved effective. However, it has now been found that riluzole, administered before or after aortic occlusion improves the neurologic status and preserves spinal cord integrity. The rabbit model of spinal cord ischemia used herein is a reliable and reproducible model for producing neurologic deficits and testing drugs that might serve to protect the spinal cord from ischemic injury. Occlusion of the infrarenal aorta for 40 minutes leads to complete paraplegia, with Tarlov scores of 0, in all control animals. To assess the impressive neuroprotective effect of riluzole, the motor function of the hind limbs was scored and the necrotic and apoptotic neuronal cell deaths associated with changes in the expression of microtubule-associated protein-2 (MAP2) cytoskeletal protein induced by ischemia were analyzed in the spinal cords of both control and treated animals.

Evidence has accumulated that the excitatory amino acids, particularly glutamate, have potent neurotoxic activity during such conditions of depleted cellular energy as hypoxia and ischemia. The ischemia-induced overaccumulation of glutamate and other excitatory amino acids in the extracellular space of the central nervous system leads to excessive excitation of the NMDA and non-NMDA receptors, leading to a rise in intracellular calcium that triggers proteases, lipases, protein kinase C, nitric oxide synthase, endonucleases, altered gene transcription, and release of free radicals, eventually producing neuronal injury and death. Much attention has recently focused on NMDA and non-NMDA receptor antagonists, which have been shown to be neuroprotective in several models of cerebral or spinal cord ischemia. Some of these prior compounds have major side effects, however, limiting their clinical use.

Riluzole (2-amino-6-trifluoromethoxy benzothiazole) is a neuroprotective drug that inhibits both sodium and calcium ion channels, activates a new class of background potassium ion channels, and blocks glutamatergic neurotransmission in the central nervous system by noncompetitively blocking the NMDA receptor. Riluzole has demonstrated anti-ischemic properties in several models of focal and global cerebral ischemia and is currently in clinical use among patients with amyotrophic lateral sclerosis. It seems devoid of major side effects, suggesting that it might be of use in clinical situations involving spinal cord ischemia.

It has been determined that riluzole administered before or after aortic occlusion was helpful in preserving the structural integrity of the spinal cord in a well-established model of severe ischemia. Furthermore, riluzole can prevent ischemia-induced apoptosis and degradation of microtubule-associated protein 2 (MAP2), a cytoskeletal protein responsible for maintaining the structural integrity of the neuron and an early marker of cytoplasmic damage induced by spinal cord injury.

Riluzole is a neuroprotective drug, although its exact molecular target has not been yet identified. An important and probably indirect effect of riluzole is the inhibition of presynaptic glutamate release. It is believed that this inhibition, which leads to a neuroprotective effect, is linked to the capacity of riluzole to inhibit both sodium and calcium ion voltage-sensitive channels and to activate a new class of background potassium ion channels that are highly expressed in the spinal cord. At the postsynaptic level riluzole should be effective on the same types of ion channels and thus prevent some of the deleterious postsynaptic effects of glutamate by opening background potassium ion channels and producing postsynaptic hyperpolarization by increasing magnesium ion blockade of NMDA receptors. In addition, administration of riluzole after spinal cord injury improves mitochondrial function and increases sodium ion-dependent glutamate reuptake.

In vivo, riluzole has demonstrated neuroprotective action in several models of neurodegenerative disease, such as Parkinson and Huntington diseases, cerebral ischemia, and traumatic spinal cord injury. It has also been reported that riluzole at the dose used in this work (8 mg/kg) attenuates both neurologic motor and cognitive dysfunction after experimental brain injury. It has now been discovered that riluzole treatment results in improved spinal cord protection in a setting of severe ischemia. The analysis of the neurologic status demonstrates that the tolerance of the spinal cord to ischemia was significantly improved by riluzole in the 3 experimental groups shown below. The best protection was obtained when riluzole was administered before ischemia; however, riluzole afforded significant protection even when administered shortly after ischemia. An intravenous injection of riluzole 30 minutes before aortic occlusion and at the onset of reperfusion led to the best Tarlov score and prevented paraplegia in almost 100% of animals, despite a 40-minute ischemic insult. Histologic examination of the spinal cords revealed either no evidence or very little evidence of injury in riluzole-treated rabbits, whereas spinal cords from control animals had evidence of extensive spinal cord injury with central gray matter necrosis, vacuolization, Niss1 substance dissolution, eosinophilic cytoplasm, and monocyte and macrophage infiltration.

Furthermore, 40 minutes of ischemia resulted in the degradation of cytoskeletal MAP2, which is known to be an early event after spinal cord injury, and that riluzole treatment totally prevented MAP2 breakdown. This observation suggests that the spinal cord really is protected against ischemia-induced necrosis. Furthermore, the ischemia induces glutamate neurotoxicity which can be prevented or reduced with administration of riluzole. This riluzole should protect neuronal tissues from glutamate neurotoxicity, regardless of the source of the glutamate.

In addition to necrosis, neuronal cell death induced by ischemia also occurred through apoptosis. Programmed cell death, or apoptosis, is defined morphologically and biochemically by cellular shrinkage, chromatin condensation, and internucleosomal fragmentation of DNA. Apoptosis is the mode of cellular death that occurs during the normal development of tissues, including the spinal cord, and it has recently been demonstrated to be an important mode of cellular death in the ischemic spinal cord. During the experiments below, apoptotic cell death was detected by the observation of positively stained nuclei with the in situ end-labeling procedure (TUNEL method). Abundant TUNEL-staining cells were observed in ischemic spinal cords 48 hours after ischemia; again, riluzole treatment prevented apoptotic cell damage. In addition to establishing that riluzole is an antiapoptotic drug, these results indirectly establish a role for glutamate in the initiation of apoptotic cell death in spinal cord neurons.

Riluzole slightly decreases body temperature when injected intravenously. It is well demonstrated that even mild hypothermia can increase the duration of ischemia tolerated by modulating the release of excitatory amino acids and by reducing the spinal cord metabolic rate for oxygen. In this study the body temperature was monitored in all animals from the moment that they were anesthetized to the moment that they were returned to their cages. All rabbits had a mild decrease in body temperature, but there was no significant difference between control and riluzole-treated animals. Hypothermia therefore does not account for the protective effects of riluzole seen in this study.

Riluzole may have important clinical implications. This drug may be administered either prophylactically to patients undergoing high-risk thoracoabdominal aortic operations or curatively to patients with a ruptured aortic aneurysm or an aortic dissection and an evolving neurologic deficit. In the latter situation, riluzole would be used to improve the neurologic outcome of patients by blocking the excitotoxic cascade in the spinal cord and by preserving numerous viable neurons while patients are undergoing emergency operation for aortic replacement and spinal cord revascularization.

Riluzole does nothing by itself to reestablish perfusion to ischemic areas. In the case of a neurologic deficit caused by aortic dissection, this drug would simply buy time until reperfusion could be established. Riluzole (100–200 mg/day) was made available for amyotrophic lateral sclerosis therapy in 1995. The drug has a few side effects, such as asthenia, mild sedative effects, and, more rarely, liver dysfunction. Some of these side effects may be more frequent at the doses of riluzole used here (8 mg/kg, or approximately 300 to 1000 mg, depending on the size of the patient), but they should not limit the clinical application of riluzole as an acute treatment in the prevention of spinal cord injury during thoracoabdominal aortic operations.

EXPERIMENTS

The infrarenal aortas of New Zealand White albino rabbits (n=40) were occluded for 40 minutes. Experimental groups were as follows: sham operation group (n=5), control group undergoing occlusion but receiving no pharmacologic intervention (n=10), experimental group A (n=10) receiving 8 mg/kg riluzole intravenously 30 minutes before ischemia, experimental group B (n=10) receiving 4 mg/kg riluzole intravenously 30 minutes before ischemia and at the onset of reperfusion, and experimental group C (n=10) receiving 8 mg/kg riluzole intravenously at the onset of reperfusion. Neurologic status was assessed at 6, 24, and 48 hours after the operation and then daily until the fifth day. All animals were sacrificed at 24, 48, or 120 hours after the operation. Spinal cords were harvested for histopathologic studies, immunohistochemical studies for microtubule-associated protein 2, and search for morphologic features of apoptosis by the terminal deoxynucleotidyltransferase-mediated deoxyuridine triphosphate-biotin nick-end labeling staining method.

We used female New Zealand White albino rabbits (Charles River Laboratories, Inc, Wilmington, Mass.) weighing 3.5 to 4.5 kg. Animal care and experiments complied with the "Guide for the Care and Use of Laboratory Animals" prepared by the Institute of Laboratory Animal Resources and published by the National Institutes of Health (NIH Publication No. 86-23, revised 1985). Animals were anesthetized by the intramuscular administration of 50 mg/kg ketamine and 10 mg/kg xylazine. Animals were allowed to breath spontaneously, and general anesthesia was maintained by inhalation of 1% halothane mixed with oxygen administered by face cone at a rate of 6 L/min. After placement of 24-gauge ear vein and artery catheters, a flank incision was made and the infrarenal aorta was exposed through a retroperitoneal approach. Intravenous heparin (150 units/kg) was given and spinal cord ischemia was induced by crossclamping of the aorta with surgical microclamps (Biover vessel clips; Arex, Palaiseau, France) for 40 minutes. Arterial blood pressure and heartbeat were continuously monitored throughout the procedure (Hewlett-Packard monitor model 78353B; Hewlett-Packard Company, Palo Alto, Calif.). Percutaneous arterial oxygen saturation was continuously monitored. Body temperature was continuously monitored with a flexible probe inserted 3 cm into the rectum. Core temperature was registered from the onset of anesthesia to 1 hour after reperfusion and supported by a heating lamp throughout the procedure. The aortic crossclamps were removed after 40 minutes and the flank was closed in 2 layers. The bladders of the paraplegic animals were emptied twice daily with the Credé maneuver. Animals in the sham operation group (n=5) were sacrificed 3 hours after exposure of the aorta without crossclamping of the vessel. Animals were randomly assigned to be sacrificed at 24, 48, or 120 hours. All animals were killed with a lethal intraperitoneal injection of 200 mg/kg pentobarbital. Spinal cords were quickly removed for histopathologic and immunohistochemical examinations. The L4-L5 segment was fixed in Holland Bouin solution. The L6-L7 segment was frozen in isopentane on dry ice and stored at $-70°$ C.

Riluzole (Research Biochemicals International, distributed by Bioblock Scientific, Illkirsch, France) was first dissolved in 0.1 N hydrochloric acid and then diluted in 0.9% saline solution. It was injected intravenously in all groups of rabbits. Experimental group A animals (n=10) received 8 mg/kg riluzole 30 minutes before aortic occlusion. Experimental group B animals (n=10) received 4 mg/kg riluzole 30 minutes before aortic occlusion and at the onset of reperfusion. Experimental group C animals received 8 mg/kg riluzole at the onset of reperfusion. Control animals (n=10) underwent standard aortic occlusion and intravenous injection of 0.9% sodium chloride 30 minutes before ischemia (volume and conditions identical to those of riluzole injection). A separate sham operation group (n=3) received 8 mg/kg riluzole to verify that the drug itself did not induce histologic changes in the spinal cord.

Neurologic status was scored by assessment of hind limb neurologic function according to the Tarlov scale (0, no movement; 1, slight movement; 2, sits with assistance; 3, sits alone; 4, weak hop; 5, normal hop) at 24, 48, or 120 hours after ischemia. Two observers (1 of whom was blinded to the experimental conditions) graded the neurologic status independently.

Statistical analyses of physiologic and hemodynamic parameters were performed by analysis of variance for repeated measures. All hemodynamic data are expressed as mean±SD. Statistical analyses of the neurologic scores were done with the nonparametric Mann-Whitney U test. Differences of $p<0.05$ were considered statistically significant.

For paraffin sections, spinal cords (L4-L5 segments) were removed and immersed in Holland Bouin solution for 24 hours. Specimens were dehydrated in alcohol 95% for 30 minutes, followed by 4 changes of 100% alcohol for 1 hour each and 5 changes of toluene for 1 hour each under vacuum at 37° C. Spinal cords were infiltrated with paraffin (4 changes of paraffin for 1 hour each) and embedded in paraffin at 57° C. under vacuum and pressure. Sections were cut on a microtome (Leica Technology BV, Rijswijk, The Netherlands) at 7 $\mu$m.

For cryostat sections, spinal cords (L6-L7 segments) were quickly extracted and freshly frozen in isopentane at 45° C. Cryostat coronal sections (10 $\mu$m) were mounted on poly-L-lysine-coated slides and tissue was postfixed by successive immersions in 0.01 mol/L phosphate-buffered saline solution (PBS) and 4% paraformaldehyde for 30 minutes. Sections were then dehydrated in ethanol baths (50%, 70%, and 100%), air dried, and stored at −70° C. until use.

All spinal cords were divided into 2 groups, 1 for frozen sections and 1 for paraffin sections. For each spinal cord studied 6 sections were placed on 3-aminopropylethoxysilane-coated slides and 10 slides per rabbit (randomly chosen) were used in each stage of the analysis. All samples processed for histopathologic and immunohistochemical experiments were taken from animals examined for functional recovery. A neuropathologist, who was blinded to experimental conditions, performed the histologic assessment by means of light microscopy.

The Klüver-Barrera Luxol fast blue staining method was used. Transverse 7 $\mu$m $\mu$m sections were deparaffinized by washing twice in xylene for 5 minutes each and heating at 56° C. overnight and were then rehydrated through a graded series of alcohols and distilled water. Sections were soaked in 70% alcohol for 10 minutes. They were stained at 57° C. for 16 hours in solution A, containing 1 mg Luxol fast blue (Solvent Blue 38; Sigma Chemical Co, St Louis, Mo.) and 5 mL 10% acetic acid in 1000 mL 95% alcohol. Sections were then rinsed in 95% alcohol and distilled water. They were differentiated by being dipped singly into 0.05% aqueous lithium carbonate solution for a few seconds, then washed through several changes of 70% alcohol, and then placed in distilled water. Sections were then counterstained with neutral red stain (Sigma). Sections were treated with 0.2% sodium bisulfite for 1 minute and then immersed in 0.1 mol/L acetate buffer (pH 5.6) for 1 minute. Neutral red staining was performed in solution B, containing 3 volumes of 0.05% neutral red stock solution and 2 volumes of 0.1 mol/L acetate buffer, for 15 minutes at room temperature. Sections were rinsed in distilled water, immersed in copper sulfate-chrome alum solution for 1 second, and rinsed in distilled water. Sections were then mounted in Aquamount (Biomeda, Foster City, Calif.).

DNA nick-end labeling by terminal deoxynucleotidyltransferase-mediated deoxyuridine triphosphate-biotin nick-end labeling (TUNEL) reaction was also used. Coronal 10 $\mu$m frozen sections were used and processed according to the TUNEL method. Sections were rehydrated in ethanol (95%, 70%, and 50%) followed by PBS and bathed in 0.3% hydrogen peroxide in methanol to inactivate endogenous peroxidase. Sections were then rendered permeable in 0.3% polysorbate and PBS and washed twice in PBS before application of the TUNEL reaction mixture (in situ cell death detection kit, distributed by Hoffman-La Roche Ltd, Basel, Switzerland). Positive control was obtained by advance incubation of a section with DNase I (20 $\mu$g/mL) for 15 minutes at room temperature before incubation with biotinylated deoxyuridine triphosphate. All slides were incubated in a humid chamber at 37° C. for 2 hours. Sections were then washed twice in PBS and allowed to incubate overnight at 4° C. with the secondary antifluorescein-peroxidase conjugate. On the following day sections were washed 3 times with PBS and the peroxidase labeling was revealed with 3-amino-9-ethyl carbazole by means of the VectaStain ABC kit (Vector Laboratories, Inc, Burlingame, Calif.). After a final rinse in distilled water, sections were coverslipped.

Frozen sections (25 $\mu$m) were immersed in 0.3% hydrogen peroxide and PBS for 10 minutes, blocked with 5% goat serum (Vector Laboratories, distributed by BIOSYS, Compiegne, France) and 3% Triton for 1 hour at room temperature, and then rinsed in PBS 1X. Sections were then incubated with the primary antibody overnight. The antiserum used for the study of cytoskeletal protein expression (microtubule-associated protein-2 [MAP2]) was a monoclonal mouse anti-MAP2 (clone HM-2, diluted 1:500; Sigma). After the primary incubation and 3 rinses in PBS 1X, sections were then incubated in biotinylated horse antimouse immunoglobulin C (diluted 1:100; Vector Laboratories) for 3 hours. MAP2 expression was visualized by 3'-diaminobenzidine and nickel chloride staining with the VectaStain ABC kit (Vector Laboratories). All sections were washed a final time, in PBS 1X and then in distilled water, and mounted with glycerol.

The results are summarized in Table I. Neurologic status was scored by assessment of hind limb neurologic functions according to the Tarlov scale (0, no movement; 1, slight movement; 2, sits with assistance; 3, sits alone; 4, weak hop; 5, normal hop). Experimental groups were as follows: sham operation group with no aortic crossclamping, control group receiving no phannacological intervention, experimental group A (n=10) receiving 8 mg/kg riluzole intravenously 30 minutes before ischemia, experimental group B (n=10) receiving 4 mg/kg riluzole intravenously 30 minutes before ischemia and at the onset of reperfusion, experimental group C (n=10) receiving 8 mg/kg riluzole intravenously at the onset of reperfusion.

TABLE I

Neurologic status at 24 hours after ischemia

| Tarlov score | Sham operation (n = 5) | Control (n = 10) | A*† (n = 10) | B*‡ (n = 10) | C§ (n = 10) |
|---|---|---|---|---|---|
| 0 | — | 10 | — | — | 1 |
| 1 | — | — | — | 1 | 3 |
| 2 | — | — | 3 | — | 1 |
| 3 | — | — | 2 | — | — |
| 4 | — | — | — | 1 | 4 |
| 5 | 5 | — | 5 | 8 | 1 |

*P = .0001 compared with control group by Mann-Whitney U test.
†P = .2004 compared with experimental group B by Mann-Whitney U test.
‡P = .0044 compared with experimental group C by Mann-Whitney U test.
§P = .0003 compared with control group by Mann-Whitney U test.

All animals in the control group became paraplegic. Except for 1 rabbit in group C, all riluzole-treated animals had better neurologic function. Luxol fast blue and terminal deoxynucleotidyltransferase-mediated deoxyuridine triphosphate-biotin nick-end labeling staining methods demonstrated typical morphologic changes characteristic of necrosis and apoptosis in control animals. Riluzole prevented or attenuated ischemia-induced necrosis, apoptosis, and cytoskeletal proteolysis, depending on the dose and the timing of administration.

At 24 hours after 40 minutes of ischemia, all rabbits in the control group (n=10) showed paralysis of the hind limbs (Tarlov score of 0). Riluzole treatment remarkably enhanced the recovery of motor function in the hind limbs. Except for 1 rabbit in group C, all animals treated with riluzole contemporaneously with ischemia demonstrated significantly better neurologic scores after reperfusion than did untreated (control) rabbits. The best result was obtained with animals that received 4 mg/kg riluzole 30 minutes before aortic occlusion and at the onset of reperfusion (group B). Eighty percent of group B animals showed intact neurologic function (Tarlov score of 5). This experimental group showed a significantly better recovery of neurologic function than that of experimental group C, which was treated with 8 mg/kg riluzole after ischemia (P<0.01).

Physiologic parameters are presented in Table II.

TABLE II

| | Physiologic parameters | | | |
|---|---|---|---|---|
| | Control (n = 10) | A (n = 10) | B (n = 10) | C (n = 10) |
| Weight (kg) | 3.92 ± 0.8 | 3.89 ± 0.9 | 4 ± 0.7 | 3.94 ± 0.8 |
| Rectal temperature* (° C.) | | | | |
| Maximum | 39.2 ± 0.5 | 39.2 ± 0.3 | 39.3 ± 0.2 | 39.4 ± 0.3 |
| Minimum | 38.3 ± 0.6 | 38.3 ± 0.3 | 38.4 ± 0.4 | 38.3 ± 0.2 |
| Heart rate (beats/min) | | | | |
| Maximum | 192 ± 7 | 195 ± 7 | 191 ± 12 | 192 ± 16 |
| Minimum | 153 ± 13 | 143 ± 14 | 142 ± 9 | 151 ± 23 |
| Mean arterial blood pressure (mm Hg) | 92 ± 14 | 93 ± 17 | 105 ± 18 | 101 ± 12 |

Values are expressed as mean ± SD. Groups are the same as given for Table I. *Maximum and minimum rectal temperatures were taken from those recorded from the onset of anesthesia to 1 hour after reperfusion.

Rectal temperature, heart rate, and mean arterial blood pressure were not affected by the administration of riluzole. There were no statistical differences in the physiologic parameters of the animals among the 4 experimental groups. Arterial oxygen saturation was within the reference range in all animals.

Klüver-Barrera and TUNEL staining methods were used to characterize necrosis and apoptosis, respectively, occurring in spinal cord injury after ischemia. FIG. 1 shows representative Klüver-Barrera staining examples observed in the white and gray matter of the spinal cord in animals sacrificed 5 days after the ischemic insult.

FIG. 1 shows representative photomicrographs of lumbar spinal cord sections stained with Klüver-Barrera stain from sham-operated rabbits (A and B), control (saline-treated) rabbits (C and D) and riluzole-treated rabbits (E and F) that underwent 40 minutes ischemia and five day reperfusion. The chosen section for illustration of the spinal cord of the riluzole treated group corresponds to a rabbit with a Tarlov score of 5, treated 30 min before aortic occlusion and at the onset of reperfusion. Normal appearance of motor neurons in the ventral horn of sham-operated rabbits is shown in A and B. Necrotic motor neurons in the ventral horn of control rabbits is shown in C and D. Ventral horn motor neurons of riluzole-treated rabbits appear completely normal.

No sign of neuronal damage was observed in the spinal cords of rabbits in the sham operation group (FIG. 1, A and B). After 40 minutes of spinal cord ischemia, typical morphologic changes characteristic of necrosis appeared in paraplegic rabbits (FIG. 1, C and D). Injured spinal cord showed invasion of white blood cells into gray and white matter, cellular disruption and vacuolization of the gray matter, presence of shrunken necrotic neurons in ventral and dorsal horn gray matter, and infiltration by polymorphonuclear neutrophils and monocytes at 5 days after ischemia. Riluzole treatment almost completely protected spinal cord against the effects of ischemia. FIG. 1, E and F, shows that signs of necrosis were not present in the spinal cords of riluzole-treated animals (group B), which appeared histologically comparable to the spinal cords of rabbits in the sham operation group.

Figure 2:
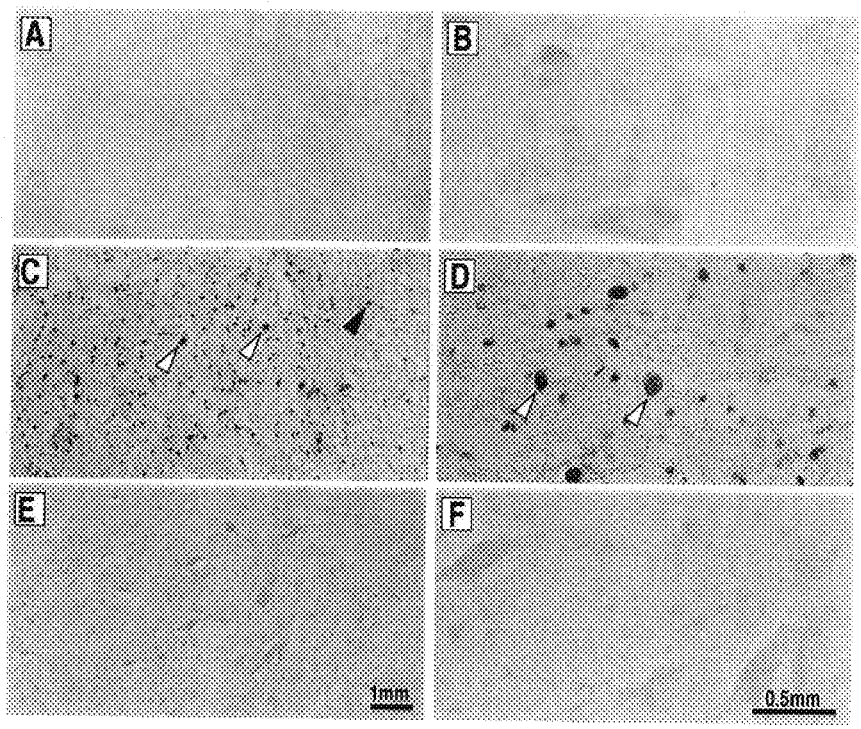
FIG. 2 is a series of photomicrographs of morphologic features of apoptosis with TUNEL staining in lumbar spinal cord sections from rabbits in sham operation (A and B), control (saline solution treatment, C and D), and experimental riluzole treatment (E and F) groups.

Apoptosis characterized by chromatin condensation, DNA fragmentation, nuclear shrinkage, and fragmentation of nuclear bodies (apoptotic bodies) was visualized by the in situ TUNEL technique. FIG. 2, C and D, shows the presence of TUNEL-staining nuclei in gray and white matter of the spinal cord 48 hours after ischemia, whereas none of the nuclei in the control preparation showed TUNEL labeling (FIG. 2, A and B).

FIG. 2 shows representative photomicrographs of morphologic features of apoptosis with TUNEL staining in lumbar spinal cord sections from rabbits in sham operation (A and B), control (saline solution treatment, C and D), and experimental riluzole treatment (E and F) groups. All but sham operation group underwent 40 minutes of ischemia and 5 days of reperfusion. Chosen section for illustration of spinal cords in riluzole-treated rabbits is that of a rabbit with Tarlov score of 5 that was treated 30 minutes before aortic occlusion and at onset of reperfusion. TUNEL-staining cells are characterized by a strong perinuclear graining pattern in gray (white arrow) and white (black arrow) matter of spinal cord. No TUNEL-staining cells could be detected in sham operation (A and B) or riluzole treatment (E and F) groups. Control rabbit spinal cords exhibited numerous TUNEL-staining neurons and glial cells in both gray and white matter (C and D).

Most TUNEL-staining neurons were located in dorsal horns and intermediate gray matter. No motor neurons were found to stain with TUNEL. Riluzole treatment significantly prevented ischemia-induced apoptosis in all sectors of the spinal cord. FIG. 2, E and F, demonstrates the lack of apoptotic nuclei in white and gray matter of the spinal cord at 48 hours of reperfusion in a riluzole-treated animal (group B). Most animals in groups A and B had no injury or minimal injury of the motor neurons, whereas 50% of the animals in group C had significant injury of the motor neurons (>50% necrotic neurons). There were no differences in the locations of TUNEL-staining neurons among animals in groups A, B, and C. However, animals in group C had more TUNEL-staining cells in intermediate gray matter and dorsal horns than did animals in groups A and B.

Figure 3:
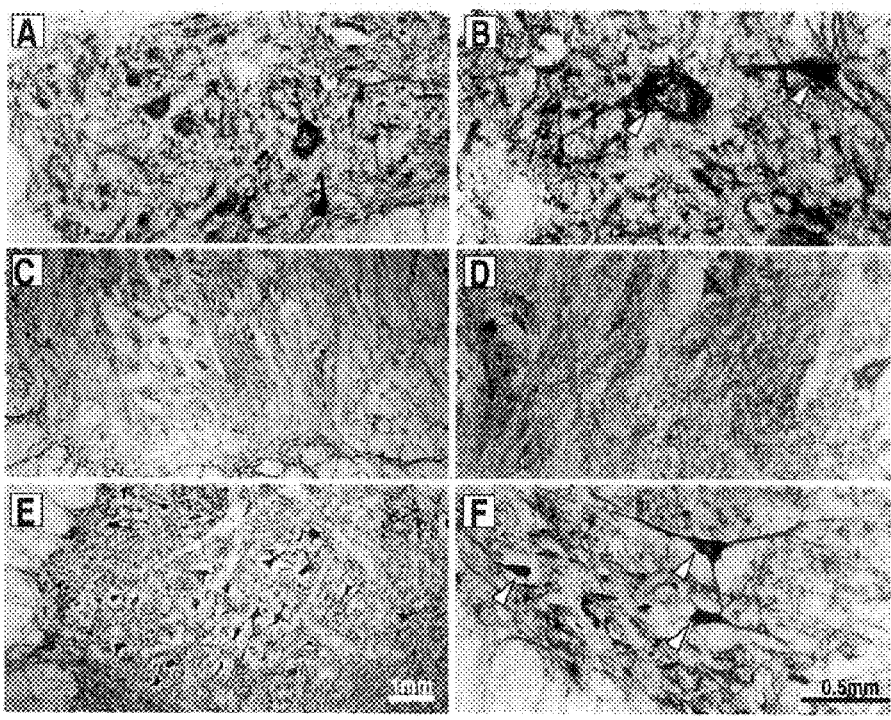
FIG. 3 is a series of photomicrographs of MAP2 immunoreactivity in lumbar spinal cord sections from rabbits in sham operation (A and B), control (saline solution treatment, C and D), and experimental riluzole treatment (E and F) groups.

The cytoskeletal element MAP2 located in neuronal soma and dendrites is involved in maintaining neuronal structural integrity, which is essential for normal cellular function and survival. Cytoskeletal degradation is highly sensitive to glutamate- and calcium ion-mediated excitotoxic events leading to activation of calcium ion-dependent phosphatases and proteases. FIG. 3, A and B, shows that the spinal cords of animals in the sham operation group exhibited intense perikaryal and dendritic MAP2 immunoreactivity.

FIG. 3 shows MAP2 immunoreactivity in lumbar spinal cord sections from rabbits in sham operation (A and B), control (saline solution treatment, C and D), and experimental riluzole treatment (E and F) groups. All but sham operation group underwent 40 minutes of ischemia and 5 days of reperfusion. Chosen section for illustration of spinal cords in riluzole-treated rabbits is that of a rabbit with Tarlov score of 5 that was treated 30 minutes before aortic occlusion and at onset of reperfusion. Intense MAP2 immunoreactivity was observed in dendrites and neuronal soma (arrow) of rabbits in sham operation (A and B) and riluzole treatment (C and D) groups. Control rabbit spinal cords (C and D) exhibited complete losses of MAP2 immunoreactivity in ventral and dorsal horns.

Aortic occlusion led to a rapid cytoskeletal protein degradation in control animals (FIG. 3, C and D.) As early as 24 hours after spinal cord ischemia there was a loss of MAP2 antigenicity in cell bodies and dendrites of ischemic spinal cord neurons in control animals (FIG. 3, C and D). Riluzole treatment prevented or attenuated the cytoskeletal proteolysis in the ischemic spinal cords, depending on the timing of administration and dose. FIG. 3, E and F, shows that in spinal cord-injured rabbits treated with riluzole, MAP2 immunoreactivity was comparable to that in animals in the sham operation group. Administration of riluzole to a separate group of rabbits that underwent sham operation (n=3) had no effect on MAP2 labeling. Thus, riluzole may have therapeutic utility during high-risk operations on the thoracoabdominal aorta.

In the clinical setting, riluzole may be administered by any convenient route. However, intravenous administration will likely be the route of choice since it is used in all emergency situations and often for anesthesia. Riluzole may be used in the prevention of perioperative spinal cord ischemia during surgery involving the descending thoracic or abdominal aorta by administering about 4 mg/kg during the induction of anesthesia (i.e. about 1 hour prior to aortic clamping. Another dose of about 4 mg/kg should be administered again at unclamping. Of course, with very long cross-clamp times, or where there is uncertainty regarding spinal cord ischemia (the impossibility of reimplanting the arteries critical for spinal cord vascularization, etc.) the dosage (about 4 mg/kg) should be repeated approximately once every 12 hours. The riluzole may also be administered intraveneously continuously at a rate of 4 mg/kg over 12 hours. This can be continued over 2 to 5 days, depending on the patient's hemodynamic status, neurological status, and the possibility of recovery. If the spinal cord is severely damaged and revascularization is not technically feasible, the use of riluzole is not justified and therefore the treatment should be suspended after three days.

In cardiac surgery, the insertion of the cannula into the aorta, clamping of the ascending aorta, manipulation or suture of the ascending aorta, microembolic phenomena (and more rarely macroembolic phenomena in about 3 to 5% of cases) are generated from the aortic wall and can migrate into the cerebral territory with predictable effects. Riluzole can be used in this instance for the prevention of the neuropsychological complications of extracorporeal circulation, especially in those patients older than 65 years of age, where there is a greater chance of a calcified and/or friable aorta and commensurately greater chance of embolism. Again a dose of about 4 mg/kg at the induction of anesthesia, and a repetition of the dose at unclamping, should be used, followed by further doses of the same amount every 12 hours for two days.

For the prevention of the neurological complications of circulatory arrest in profound hypothermia during surgery of the aortic arch, a dose of 4 mg/kg should be administered at induction of anesthesia, and again upon cerebral recirculation (generally 2 to 4 hours later). Where the circulatory arrest is brief (i.e. less than 30 minutes), doses should be continued every 12 hours for two days. Where the circulatory arrest is longer than 30 minutes (and especially over 45 minutes), the 12 hour dosing should be continued for five days.

For the prevention of cerebral ischemia in high-risk carotid surgery (bilateral stenosis greater than 70%, or occlusion of one carotid artery and stenosis greater than 70% of the other carotid artery, for instance) a dose of 4 mg/kg may be administered upon induction of anesthesia, and again upon unclamping of the carotid artery. If the EEG did not change during the clamping, no further action is necessary. If the EEG changed or exhibited disturbances during clamping, doses of 4 mg/kg may be continued every 12 hours for 5 days to minimize the effect of the cerebral ischemia.

For the treatment of spinal cord ischemia (neurological deficit in process of establishment) or cerebral ischemia upon aortic dissection or aortic rupture, 4 mg/kg should be administered in advance of aortic repair and spinal cord or cerebral revascularization. The dose is administered at induction of anesthesia, again upon aortic unclamping, and at 12 hour intervals over the following 5 days.

What is claimed is:

1. A method for the reduction of glutamate neurotoxicity in the pathophysiology of spinal cord injury induced by aortic cross-clamping comprising administering to a patient, riluzole in an amount effective to reduce glutamate neurotoxicity, contemporaneously with aortic cross-clamping.

2. The method of claim 1 wherein the riluzole is administered prior to said aortic cross-clamping.

3. The method of claim 1 wherein the riluzole is administered after said aortic cross-clamping.

4. The method of claim 1 wherein the riluzole is administered in an amount between about 4–8 mg/kg body weight of said patient.

5. A method for the reduction of spinal cord injury resulting from ischemia comprising administering to a patient, riluzole in an amount effective to reduce spinal cord injury, contemporaneously with ischemia.

6. The method of claim 5 wherein the riluzole is administered prior to said ischemia.

7. The method of claim 6 wherein riluzole is administered before aortic occlusion and at the onset of perfusion.

8. The method of claim 5 wherein the riluzole is administered in an amount between about 4 and about 8 mg/kg body weight of said patient.

9. A method for reducing the effects of ischemia on neuronal tissues comprising administering to a patient, riluzole in an amount effective to reduce the effects of ischemia, contemporaneously with said ischemia.

10. The method of claim 9 wherein the riluzole is administered prior to said ischemia.

11. The method of claim 9 wherein the riluzole is administered at the onset of reperfusion.

12. The method of claim 11 wherein the riluzole is administered in an amount between about 4 and about 8 mg/kg body weight of said patient, during each administration.

13. A method for preserving neuronal tissues against the effects of glutamate neurotoxicity comprising contacting said neuronal tissues with riluzole contemporaneously with exposure of said tissues to glutamate.

14. The method of claim 13 wherein the riluzole is administered prior to exposure of said tissues to glutamate.

15. The method of claim 13 wherein the riluzole is administered in an amount of from about 300 to about 1000 mg.

16. A method for the reduction of glutamate neurotoxicity in pathophysiology of spinal cord injury comprising administering prophylactically or curatively to a patient, riluzole in an amount effective to reduce glutamate neurotoxicity.

17. The method of claim 1 wherein the spinal cord injury is induced by aortic occlusion.

18. The method of claim 17 wherein the riluzole is administered prior to aortic occlusion.

19. The method of claim 18 wherein administering of riluzole is before aortic occlusion and at the onset of reperfusion.

20. A method of claim 16 wherein the riluzole is administered curatively to a patient with a ruptured aortic aneurysm, or an aortic dissection, or a traumatic aortic rupture.

21. The method of claim 6 wherein the riluzole is administered in an amount of from about 300 to about 1000 mg.

22. The method of claim 1 wherein the riluzole administration is repeated.

23. The method of claim 1 wherein the riluzole is administered both before said aortic cross-clamping and after reperfusion.

24. The method of claim 5 wherein the riluzole is further administered after said ischemia.

25. The method of claim 16 wherein the riluzole is administered curatively to the patient.

* * * * *